United States Patent
Kim et al.

(10) Patent No.: US 12,102,666 B2
(45) Date of Patent: Oct. 1, 2024

(54) USE OF RECOMBINANT ANTIBACTERIAL PROTEIN ABLYSIN FOR EFFECTIVELY KILLING MULTIDRUG-RESISTANT PATHOGENIC BACTERIA

(71) Applicant: KYUNGPOOK NATIONAL UNIVERSITY INDUSTRY-ACADEMIC COOPERATION FOUNDATION, Daegu (KR)

(72) Inventors: Jung Min Kim, Daegu (KR); Jong Sook Jin, Daegu (KR); Shukho Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 753 days.

(21) Appl. No.: 17/281,952

(22) PCT Filed: Jul. 2, 2020

(86) PCT No.: PCT/KR2020/008653
§ 371 (c)(1),
(2) Date: Mar. 31, 2021

(87) PCT Pub. No.: WO2021/002697
PCT Pub. Date: Jan. 7, 2021

(65) Prior Publication Data
US 2021/0353720 A1    Nov. 18, 2021

(30) Foreign Application Priority Data
Jul. 3, 2019  (KR) .................. 10-2019-0080097

(51) Int. Cl.
| | | |
|---|---|---|
| *A61K 38/47* | (2006.01) | |
| *A01N 63/50* | (2020.01) | |
| *A23C 9/152* | (2006.01) | |
| *A23K 20/147* | (2016.01) | |
| *A23K 20/195* | (2016.01) | |
| *A23L 3/3463* | (2006.01) | |
| *A23L 3/3526* | (2006.01) | |
| *A23L 33/10* | (2016.01) | |
| *A23L 33/175* | (2016.01) | |
| *A61P 31/04* | (2006.01) | |
| *A01P 1/00* | (2006.01) | |

(52) U.S. Cl.
CPC .............. *A61K 38/47* (2013.01); *A01N 63/50* (2020.01); *A23C 9/1526* (2013.01); *A23K 20/147* (2016.05); *A23K 20/195* (2016.05); *A23L 3/34635* (2013.01); *A23L 3/3526* (2013.01); *A23L 33/127* (2016.08); *A23L 33/175* (2016.08); *A61P 31/04* (2018.01); *A01P 1/00* (2021.08); *A23V 2002/00* (2013.01)

(58) Field of Classification Search
CPC ...... A61K 38/47; A61K 38/164; A01N 63/50; A01N 37/44; A23C 9/1526; A23K 20/147; A23K 20/195; A23K 10/16; A23L 3/34635; A23L 3/3526; A23L 33/127; A23L 33/175; A23L 33/17; A61P 31/04; A61P 31/02; A01P 1/00; A23V 2002/00; C07K 14/212; Y02A 50/30
See application file for complete search history.

(56) References Cited

U.S. PATENT DOCUMENTS

| | | |
|---|---|---|
| 6,562,958 B1 | 5/2003 | Breton et al. |
| 10,905,749 B2 * | 2/2021 | Howell .................. A01N 63/00 |
| 2017/0216410 A1 * | 8/2017 | Howell .................. A61L 27/54 |
| 2018/0078619 A1 | 3/2018 | Park et al. |

FOREIGN PATENT DOCUMENTS

| | | |
|---|---|---|
| KR | 10-2016-0118994 A | 10/2016 |
| WO | 02-077183 A2 | 10/2002 |
| WO | 2017-040499 A1 | 3/2017 |
| WO | WO-2019118632 A1 * | 6/2019 ........... A61K 38/162 |

OTHER PUBLICATIONS

Doron ("Bacterial infections: Overview"; International Encyclopedia of Public Health, 2008:273-282 (Year: 2008).*
NCBI GenPept, GenBank: ADX01849.1, Lyzozyme M1 (1,4-beta-N-acetylmuramidase) [Acinetobacter baumannii 1656-2], www.ncbi.nlm.nih.gov/protein/322506395 (Year: 2014).*
NCBI GenBank Accession No. WP_000163500.1 Multispecies glycoside hydrolase family 25 protein, *Acinetobacter*, Jun. 2, 2019 (on IDS submitted Mar. 31, 2021) (Year: 2019).*
Pérez-Dorado, et al. "Insights into pneumococcal fratricide from the crystal structures of the modular killing factor LytC." Nature structural & molecular biology vol. 17,5 (2010): 576-81. doi:10.1038/nsmb.1817 (Year: 2010).*
International Search Report for PCT/KR2020/008653 mailed Dec. 1, 2020 from Korean Intellectual Property Office.
(Continued)

*Primary Examiner* — Terry A McKelvey
*Assistant Examiner* — Andrew T Moehlman
(74) *Attorney, Agent, or Firm* — Revolution IP, PLLC

(57) ABSTRACT

The present invention relates to a method of using a recombinant antibacterial protein, termed Ablysin, for effectively killing multidrug-resistant pathogenic bacteria. The recombinant protein Ablysin is administered to prevent or treat infectious diseases caused by the antibiotic-resistant bacteria *Acinetobacter baumannii*. Ablysin can be widely used in antibiotics, disinfectants, food additives, feed additives, and the like. In particular, the Ablysin protein uses peptidoglycan, a component of the cell wall of bacteria, as a substrate and exhibits bacterial killing ability due to peptidoglycan degradation. The Ablysin of the present invention can be applied in the pharmaceutical industry, food industry, biotechnology, or similar industries, as the protein effectively kills bacteria at a desired place or in a target substance without problems of resistance that occurs in other antimicrobial agents.

1 Claim, 3 Drawing Sheets

Specification includes a Sequence Listing.

(56) References Cited

OTHER PUBLICATIONS

NCBI. GenBank Accession No. WP_000163500.1. Multispecies: glycoside hydrolase family 25 protein, *Acinetobacter*, Jun. 2, 2019.
Weber, B. S. et al., "Genetic Dissection of the Type VI Secretion System in Acinetobacter and Identification of a Novel Peptidoglycan Hydrolase, TagX, Required for Its Biogenesis", mBio. 2016, vol. 7, No. 5, thesis No. e01253-16, pp. 1-17.
Huang, G. et al., "Antibacterial properties of Acinetobacter baumannii phage Abp1 endolysin (PlyAB1)", BMC Infectious Disease. 2014, vol. 14, thesis No. 681, pp. 1-8.
Garcia-Quintanilla, M. et al., "Activity of Host Antimicrobials against Multidrug-Resistant Acinetobacter baumannii Acquiring Colistin Resistance through Loss of Lipopolysaccharide", Antimicrob Agents Chemother. 2014, vol. 58, No. 5, pp. 2972-2975.
Michael G Smith et al., "New insights into Acinetobacter baumannii pathogenesis revealed by high-density pyrosequencing and transposon mutagenesis", Genes & Development, Cold Spring Harbor Laboratory Press, Plainview, NY, US, vol. 21, No. 5, Mar. 1, 2007 (Mar. 1, 2007), pp. 601-614.
Anonymus: "Database Identifier Version Organism First seen Last seen Activ", May 25, 2017 (May 25, 2017), XP055928622, Retrieved from Internet: URL:https://www.uniprot.org/uniparc/UPI000A38FB14.

* cited by examiner

[FIG. 1]

HHHHHHGMTKLAKTFSAPRYNTLIGIVLACVMGVLTYFGLFYQQKAIAQDYPV
QGFDVSHHQENINWKKISPKKFQFVYLKATEGGDYKDPKFQENWLKAREHGFH
VGAYHFYRLCRDGKTQAENFISTVPNKADALPPVIDLEYDSNCINSHTKEQLLKE
IGIMHDSLKHHYGKQPIFYISKTFYHIVLIGSFPHTPLWVRDYEGKPELKDKRKW
LFWQHSNQGKIEGITKPVDLNVYEGSVKEWHQFLQQQGIVKAQ (SEQ ID NO: 1)

[FIG. 2]

catcatcatcatcatggtatgaccaagctggcaaaaaccttttctgcaccacgctacaatacccttattgggattgtttt
agcttgtgttatgggggttctcacctacttcggtctgttctaccagcaaaaagctattgctcaagattacccagttcaaggc
tttgatgtctctcaccatcaagaaaatattaactggaaaaaaatatcacccaaaaaattccagttcgtctatttaaaagcgac
tgaaggcggtgattataaagatccaaaattcaagaaaactggttaaaagcacgcgaacatggctttcatgtcggggctt
atcatttttatcgtttatgtcgtgatggcaaaacacaagctgaaaattttatttcaaccgtacccaacaaagctgatgccctt
cctcccgttattgatctggaatatgacagcaactgtattaattctcataccaaagaacaattacttaaagaaataggcatcat
gcatgacagcttaaagcatcattatggtaaacagcctatctttatatttccaaaactttttaccatattgtattaataggtagt
ttccctcatacacctctttggggtcagagattacgaagggaaacctgagctgaaagacaagcgaaaatggctcttttggca
gcatagtaatcaaggtaaaattgaaggcatcaccaagccagtagacttaaatgtttatgaaggttcagtcaaagaatggc
accaattttacagcagcaaggcatcgtgaaagcacaatga (SEQ ID NO: 2)

[FIG. 3]
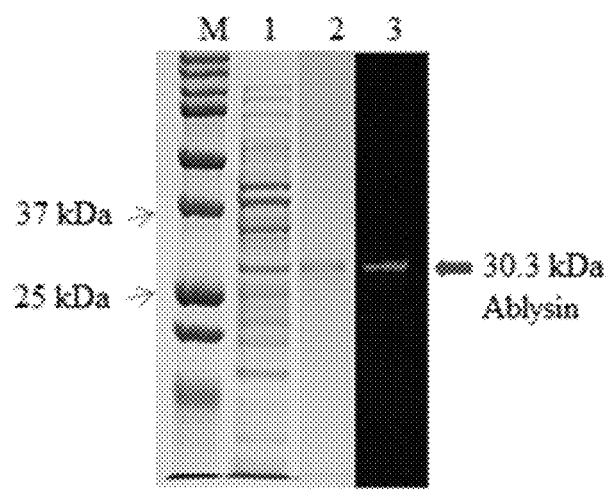

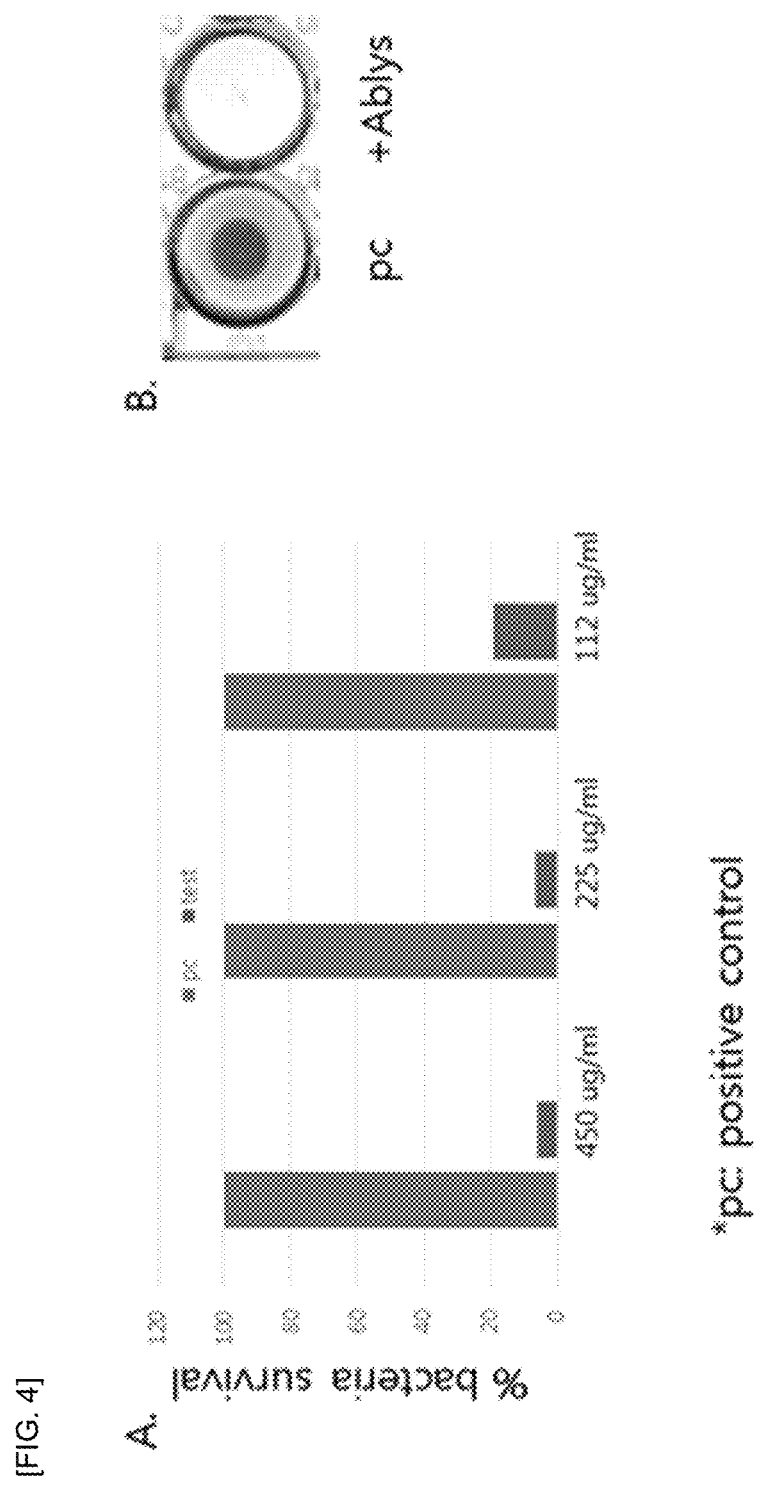
[FIG. 4]

USE OF RECOMBINANT ANTIBACTERIAL PROTEIN ABLYSIN FOR EFFECTIVELY KILLING MULTIDRUG-RESISTANT PATHOGENIC BACTERIA

CROSS REFERENCE TO PRIOR APPLICATIONS

This application is the 35 U.S.C. 371 national stage of International application PCT/KR2020/008653 filed on Jul. 2, 2020; which claims priority to Korean Patent Application No. 10-2019-0080097 filed on Jul. 3, 2019. The entire contents of each of the above-identified applications are hereby incorporated by reference.

TECHNICAL FIELD

The present invention relates to a use of a recombinant antibacterial protein Ablysin that effectively kills multidrug-resistant pathogenic bacteria, and more specifically to a pharmaceutical composition for preventing or treating infectious diseases comprising the recombinant antibacterial protein Ablysin as an active ingredient, and to antibiotics, disinfectant, a food additive, or a feed additive comprising the antibacterial protein as an active ingredient, which effectively kills multidrug-resistant gram-negative bacteria of *Acinetobacter baumannii, Klebsiella pneumoniae, Escherichia coli, Pseudomonas aeruginosa* and multidrug-resistant gram-positive bacteria of *Staphylococcus aureus* and *Enterococcus faecium*.

BACKGROUND ART

As the resistance of pathogenic bacteria to antimicrobial agent increases due to misuse and abuse of antimicrobial agents, the number of cases that are difficult to treat with antibiotics has increased significantly, resulting in a serious health problem, and the development of new antimicrobial agents to cope with this is urgently needed.

As a new antibacterial drug that is drawing attention, bacteriophage lysin, which degrades the bacterial wall and kills bacterial cells, is being developed as an antibacterial agent and thus its biological data are accumulating, and efforts to use the data and develop better antimicrobial agents are continuing.

The lysin antimicrobial proteins developed so far were produced and purified biotechnologically, and the effect of killing bacteria was expected by treating the target bacteria, but there was a limitation showing the killing effect only for gram-positive bacteria. The reason that the effect of antibacterial protein of a medicine prepared from lysin against gram-negative bacteria is insufficient is that when the purified antimicrobial proteins are treated with bacteria, the outer membrane prevents the antimicrobial protein from reaching the peptidoglycan layer which is a target substance for antibacterial proteins prepared from lysin, due to the structure of the cell wall of gram-negative bacteria and thus does not exhibit effective antimicrobial activity. Therefore, the antibacterial protein prepared from lysin, which has effective killing ability against gram-negative bacteria, is a very promising antibacterial agent.

Among gram-negative bacteria, carbapenem-resistant Acinetobacter baumannii (CRAB) is the top priority bacterium in the world due to its highest prevalence and mortality rate, making it essential to treat it as a top priority.

The World Health Organization (WHO) designated CRAB as one of the most dangerous bacteria in the 21st century and reported that the development of a therapeutic agent was urgent. Patients having immunosuppression, chronic lung disease and adult chronic disease are very susceptible to infection by CRAB, and long-term hospitalized patients can be in very critical condition from pneumonia, bloodstream infection, and wound infection. Accordingly, a recombinant protein having an antibacterial action on both gram-positive bacteria and gram-negative bacteria can be widely used as an antibacterial agent to treat multidrug-resistant CRAB bacterial infections.

DISCLOSURE

Technical Problem

An object of the present invention is to provide a pharmaceutical composition for preventing or treating multidrug-resistant pathogenic bacterial infectious diseases comprising Ablysin protein as an active ingredient.

Another object of the present invention is to provide antibiotics, disinfectant, a food additive and a feed additive for killing multidrug-resistant pathogenic bacteria comprising Ablysin protein as an active ingredient.

Technical Solution

In order to achieve the above object, the present invention provides a pharmaceutical composition for preventing or treating multidrug-resistant pathogenic bacterial infectious diseases comprising an Ablysin protein, wherein the Ablysin protein comprises an amino acid sequence represented by SEQ ID NO: 1 as an active ingredient.

Also, the present invention provides an antibiotic for killing multidrug-resistant pathogenic bacteria comprising an Ablysin protein, wherein the Ablysin protein comprises an amino acid sequence represented by SEQ ID NO: 1 as an active ingredient.

In addition, the present invention provides a disinfectant for killing multidrug-resistant pathogenic bacteria comprising an Ablysin protein, wherein the Ablysin protein comprises an amino acid sequence represented by SEQ ID NO: 1 as an active ingredient.

Furthermore, the present invention provides a food additive for killing multidrug-resistant pathogenic bacteria comprising an Ablysin protein, wherein the Ablysin protein comprises an amino acid sequence represented by SEQ ID NO: 1 as an active ingredient.

In addition, the present invention provides a feed additive for killing multidrug-resistant pathogenic bacteria comprising an Ablysin protein, wherein the Ablysin protein comprises an amino acid sequence represented by SEQ ID NO: 1 as an active ingredient.

Advantageous Effects

The present invention relates to the use of the recombinant antibacterial protein Ablysin to effectively kill multidrug-resistant pathogenic bacteria. The recombinant protein Ablysin of the present invention exhibits apoptosis against antibacterial agent-resistant *Acinetobacter baumannii, Klebsiella pneumoniae, Escherichia coli, Pseudomonas aeruginosa, Staphylococcus aureus* and *Enterococcus faecium* to prevent or treat infectious diseases caused by these bacteria and thus it can be widely used in antibiotics, disinfectants, food additives, feed additives, and the like. In particular, the Ablysin uses peptidoglycan, which is a component of the cell wall of bacteria, as a substrate, and exhibits bacterial killing ability due to peptidoglycan degradation. The peptidoglycan exists only in bacteria and not in humans or animals, and thus there is an advantage that Ablysin of the present invention is safe because it does not affect humans and animals, and can be applied to the pharmaceutical industry, food industry, biotechnology, etc., as well as can effectively kill bacteria in a target place or a target substance without problems of resistance to multi-drug antimicrobial agents.

DESCRIPTION OF DRAWINGS

FIG. 1 shows the amino acid sequence of the Ablysin, an antibacterial protein derived from a bacterial strain having antibacterial activity (The underlined part is a sequence of 6 histidine amino acids artificially added for protein purification.).

FIG. 2 shows the nucleotide sequence of the Ablysin.

FIG. 3 shows image of SDS-PAGE analysis after protein purification of the Ablysin, which was confirmed by performing western analysis using a specific antibody that recognizes the six histidine amino acid sequences of Ablysin.

FIG. 4 shows the ability of the Ablysin to kill against multidrug-resistant *Acinetobacter baumannii* 1656-2 strain.

BEST MODE

Accordingly, the inventors of the present invention transformed DNA encoding a recombinant protein (referred to as Ablysin) together with a vector in *E. coli* to express the protein, and confirmed that the protein exhibited killing activity in *Acinetobacter baumannii, Klebsiella pneumoniae, Escherichia coli, Pseudomonas aeruginosa, Staphylococcus aureus* and *Enterococcus faecium* and thus it can be used as an alternative antimicrobial agent for *Acinetobacter baumannii* bacteria, which is the most serious infection problem in hospital, and completed the present invention.

The present invention provides a pharmaceutical composition for preventing or treating multidrug-resistant pathogenic bacterial infectious diseases comprising an Ablysin protein, wherein the Ablysin protein comprises an amino acid sequence represented by SEQ ID NO: 1 as an active ingredient.

Specifically, the Ablysin protein may be derived from *Acinetobacter baumannii* 1656-2 (KCTC 18184P), but it is not limited thereto. The present inventors isolated the bacteria from temporary specimens of hospital-infected patients, and deposited the isolated bacteria to the Korea Human Gene Bank (KHGB) of the Korea Research Institute of Bioscience & Biotechnology (KRIBB) on Nov. 20, 2009 (accession number KCTC 18184P).

Specifically, the gene encoding the Ablysin protein may comprise a nucleotide sequence represented by SEQ ID NO: 2, but it is not limited thereto.

In detail, the multidrug-resistant pathogenic bacteria may be *Acinetobacter baumannii, Klebsiella pneumoniae, Escherichia coli, Pseudomonas aeruginosa, Staphylococcus aureus* or *Enterococcus faecium*, but it is not limited thereto.

Specifically, the multidrug-resistant pathogenic bacterial infectious disease may be sepsis, pneumonia, food poisoning, infection, impetigo, purulent disease, acute dermatitis, wound infection, bacteremia, endocarditis or enteritis, but it is not limited thereto.

The Ablysin protein of the present invention uses peptidoglycan, which is a component of the cell wall of bacteria, as a substrate to degrade and disrupt the cell wall, thereby killing the bacteria. The peptidoglycan exists only in bacteria and not in humans or animals, and thus there is an advantage that Ablysin of the present invention is safe because it does not affect humans and animals, and can be applied to the pharmaceutical industry, food industry, biotechnology, etc., as well as can effectively kill bacteria in a target place or a target substance without problems of resistance to multi-drug antimicrobial agents.

As used herein, the term 'treatment' refers to the prevention, inhibition and alleviation of infectious diseases caused by multidrug-resistant pathogenic bacteria.

When the composition of the present invention is a pharmaceutical composition, for administration, it may include a pharmaceutically acceptable carrier, excipient or diluent in addition to the above-described active ingredients. Examples of the carrier, excipient and diluent include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oils.

The pharmaceutical compositions of the present invention can be formulated and used in the form of oral formulations such as powders, granules, tablets, capsules, suspensions, emulsions, syrups, aerosols, external preparations, suppositories, or sterile injectable solutions according to a conventional method. In detail, when formulated, it may be prepared using diluents or excipients such as fillers, weighting agents, binders, wetting agents, disintegrants and surfactants that are commonly used. Solid preparations for oral administration include tablets, pills, powders, granules, capsules, and the like, but they are not limited thereto. Such a solid preparation may be prepared by mixing at least one excipient, for example, starch, calcium carbonate, sucrose, lactose, gelatin, etc. in addition to the active ingredient. Further, in addition to simple excipients, lubricants such as magnesium stearate and talc may also be used. It can be prepared by adding various excipients such as wetting agents, sweetening agents, fragrances, preservatives, and the like, in addition to liquids and liquid paraffins for oral use. Formulations for parenteral administration include sterile aqueous solutions, non-aqueous solvents, suspensions, emulsions, lyophilized formulations, and suppositories. As the non-aqueous solvent and suspending agent, propylene glycol, polyethylene glycol, vegetable oil such as olive oil, injectable ester such as ethyl oleate, and the like may be used. As a base for suppositories, witepsol, macrosol, TWEEN-61™ (polyethylene glycol sorbitan monostearate), cacao butter, laurin, glycerogelatin, and the like may be used.

A suitable dosage of the pharmaceutical composition of the present invention varies depending on the condition and weight of the patient, the severity of the disease, the form of the drug, and the time, but can be appropriately selected by a person skilled in the art. Thus, the daily dosage of the pharmaceutically acceptable salt is preferably 0.001 mg/kg to 50 mg/kg, and may be administered once to several times a day as necessary.

In addition, the present invention provides an antibiotic for killing multidrug-resistant pathogenic bacteria comprising an Ablysin protein, wherein the Ablysin protein comprises an amino acid sequence represented by SEQ ID NO: 1 as an active ingredient.

As used herein, the term "antibiotics" refers to cosmetic or pharmaceutical preservatives, fungicides and antibacterial agents.

Cosmetics contain oil or water as their main components, and because there are many combinations of glycerin or sorbitol as carbon sources of microorganisms, amino acid derivatives and proteins as nitrogen sources, it is easy for microorganisms such as bacteria. In addition, it can be said that the risk of contamination by microorganisms is much greater because the period of use is very long compared to that of food. It is essential to add an antibacterial agent to protect cosmetics for a long time from discoloration or deodorant caused by microbial contamination due to use.

The Ablysin protein of the present invention has excellent ability to kill a wide range of bacteria compared to conventional antimicrobial agents. If the protein is used as an antimicrobial agent, unlike conventional antimicrobial agents, it has the advantage of not inducing tolerance or resistance of bacteria to provide an antibiotic material having a longer life cycle compared to the conventional antibiotic material. While most of the antibiotics face increased resistance, the range of use decreases, whereas the antimicrobial agent comprising the protein of the present invention as an active ingredient can fundamentally solve the problem of resistance to antibacterial agents, thereby increasing the product lifespan as an antimicrobial agent.

Therefore, an antibiotic comprising the protein of the present invention having killing activity to multidrug-resistant pathogenic bacteria as an active ingredient can be usefully used as an antibiotic having excellent antibacterial, bactericidal and antiseptic effects.

In addition, the present invention provides a disinfectant for killing multidrug-resistant pathogenic bacteria comprising an Ablysin protein, wherein the Ablysin protein comprises an amino acid sequence represented by SEQ ID NO: 1 as an active ingredient.

The disinfectant comprising the Ablysin protein of the present invention having the ability to selectively kill multidrug-resistant pathogenic bacteria as an active ingredient can be usefully used as a disinfectant for hospitals and health care to prevent hospital infection, and also as a disinfectant for general life, food and cooking places and facilities, livestock housing in the livestock industry.

In addition, the present invention provides a food additive for killing multidrug-resistant pathogenic bacteria comprising an Ablysin protein, wherein the Ablysin protein comprises an amino acid sequence represented by SEQ ID NO: 1 as an active ingredient.

Food additives of the present invention may contain preservatives, fungicides, antioxidants, spices, seasonings, sweeteners, flavoring agents, expanding agents, reinforcing agents, improving agents, emulsifying agents, various nutrients, synthetic flavoring agents such as synthetic flavoring agents and natural flavoring agents, colorants, coloring agents, fillers (cheese, chocolate etc.), pectic acid and its salts, alginic acid and its salts, organic acids, protective colloid thickeners, pH adjusting agents, stabilizers, antifoaming agents, solvents, release agents, preservatives, quality improving agents, glycerin, alcohols, carbonating agents used in carbonated drinks, and the like, which are additionally added to food, and can be added by dipping in, spraying to or mixing with food.

In addition, the present invention provides a feed additive for killing multidrug-resistant pathogenic bacteria comprising an Ablysin protein, wherein the Ablysin protein comprises an amino acid sequence represented by SEQ ID NO: 1 as an active ingredient.

The Ablysin protein of the present invention can be used as an additive for livestock feed and drinking water for livestock for the purpose of preventing or treating bacterial infections and can improve or maintain animal feed intake, growth, feed efficiency, survival rate, feeding condition, production capacity, etc.

As described in the present invention, "multidrug-resistant pathogenic bacteria" include *Acinetobacter baumannii*, *Klebsiella pneumoniae*, *Escherichia coli*, *Pseudomonas aeruginosa*, *Staphylococcus aureus* and *Enterococcus faecium*, but it is not limited thereto.

Hereinafter, the present invention will be described in more detail through examples. These examples are only intended to illustrate the present invention in more detail, and it will be apparent to those skilled in the art that the scope of the present invention is not limited by these examples according to the gist of the present invention.

<Example 1> Preparation and Purification of Recombinant Protein Ablysin

In order to obtain a region encoding a lysozyme-like protein of *Acinetobacter baumannii* 1656-2 (Accession No. KCTC 18184P), gDNA of 1656-2 bacteria was extracted. A polymerase chain reaction (PCR) was performed using the gDNA as a template, and the primers used were as follows: ablys F: 5'-CATCATCATCATCATCATGGTATGAC-CAAGCTGGCAAAAACCT-3'(SEQ ID NO: 3), ablys R: 5'-CGTTCTGATTTAATCTGTATCATTGTGCTTTCAC-GATGCCTTG-3'(SEQ ID NO: 4). The PCR fragment (800 bp) was obtained by eluting a band of a desired size after electrophoresis on an agarose gel.

An expression vector (pBAD-HIS-a) was amplified using primers vector F: 5'-TGATACAGAT-TAAATCAGAACGCAGAAGCG-3'(SEQ ID NO: 5), and vector R: 5'-ACCATGATGATGATGATGATGAGAACCC-3'(SEQ ID NO: 6) to obtain a PCR fragment of 3950 bp and the 3950 bp PCR fragment and 800 bp gene were ligated by an isothermal DNA assembly method (GIBSON ASSEMBLY®).

*E. coli* TOP10 was transformed with the prepared vector (Ablysin-pBAD), and then cultured in LB liquid medium to which 100 µg/ml of ampicillin was added, until the absorbance of the bacteria became 0.5 (600 nm wavelength). Next, L-arabinose was added so that the final concentration was 0.2 mM, followed by incubation at 18° C. for 16 hours to induce protein expression.

Thereafter, after harvesting the bacteria, the bacteria were disrupted with a lysis buffer [50 mM Tris-HCl pH 8.0, 200 mM NaCl, 100 µM $ZnCl_2$] and an ultrasonic sonicator. The crushed bacterial lysate was centrifuged to take a supernatant, and injected into a Ni-NTA column, Ablysin proteins tagged with six histidines at the N-terminus were purified using elution buffer [500 mM imidazole, 50 mM Tris-Cl (pH 8.0), 200 mM NaCl, 100 µM $ZnCl_2$].

To confirm the purified Ablysin protein, after performing SDS-PAGE (12%) and Coomassie blue staining, Ablysin protein was confirmed at 30.3 kDa as shown in FIG. 3 and Western analysis using an anti-6×His monoclonal antibody confirmed that the 30.3 kDa protein was 6×His tagged Ablysin.

In FIG. 3, M is a protein size marker, 1 is a bacterial lysate, 2 is a fraction sample obtained by harvesting Ablysin on a Ni-NTA column, and 3 is a Western test result using an anti-6×His monoclonal antibody for Ablysin.

The amino acid sequence and number of Ablysin is composed of 259 amino acids including histidine tag as shown in FIG. 1 and has a total size of 30.3 kDa. The gene coding sequence is 778 bp as shown in FIG. 2.

<Example 2> Analysis of Ability of Ablysin to Kill Bacteria

The bacterial killing ability of Ablysin for gram-negative *Acinetobacter Baumannii* 1656-2 strain 1656-2, which is a multidrug clinical strain, was performed as follows (FIG. 4). Each bacterium was prepared to have a bacterial number of $5 \times 10^4$ CFU/well using Luria Bertani (LB) broth, and the purified Ablysin protein was added to 450, 225, and 112 ug/ml, respectively and reacted at 35° C. for 16 hours and then, the growth degree (turbidity) of the bacteria was observed.

As a result, growth of bacteria was observed in all the control groups (pc) in the well plate, whereas in the test group (+Ablysin), it was confirmed that *Acinetobacter baumannii* showed a transparent liquid in which no growth of bacteria was observed at an enzyme amount of 112 ug/ml or more, and thus had a killing effect (FIG. 4A). Even when observed with the naked eye, the growth of bacteria was observed as a thick precipitate in the well in the control group (pc), whereas it was found to be transparent in the test group (+Ablysin) (FIG. 4B).

As described above, the minimum inhibitory concentration of Ablysin was determined by the same method for 16 weeks using 6 subspecies *Acinetobacter baumannii* (ST357, ST208, ST552, ST191, ST369, ST229), which are clinical isolates prevalent in Korean hospitals and resistant to carbapenem-based antibiotics. As a result, the MIC value of 110-230 ug/ml was shown (Table 1).

TABLE 1

| *Acinetobacter baumannii* Sequencing type (ST) | Strain | MIC (ug/mL) Ablysin |
| --- | --- | --- |
| ST357 | 003 (20130567) | 230 |
|  | 004 (20130721) | 230 |
|  | 006 (20130976) | 230 |
| ST208 | 011 (20132370) | 230 |
|  | 012 (20132411) | 230 |
|  | 013 (20132512) | 230 |
| ST552 | 015 (20133395) | 230 |
| ST191 | 009 (20131909) | 230 |
|  | 017 (20134542) | 230 |
|  | 027 (20136764) | 230 |
| ST369 | 039 (20137924) | 110 |
|  | 041 (20138989) | 110 |
|  | 046 (20140444) | 110 |
| ST229 | 070 (20144539) | 230 |
|  | 079 (20145719) | 230 |
|  | 080 (20145805) | 230 |

The minimum inhibitory concentration of Ablysin was measured for carbapenem-resistant *Klebsiella pneumoniae* 20 strains, oxacillin-resistant *Staphylococcus aureus* 20 strains, carbapenem and cephalosporin multidrug-resistant *E. coli* 20 strains, carbapenem-resistant *Pseudomonas aeruginosa* 20 strains, and vancomycin-resistant *Enterococcus faecium* 20 strains. As a result, the antibacterial effect on all of them was found to be 450 ug/ml concentration (MIC) (Table 2). For reference, the above clinically isolated bacteria were sold and used by the National Culture Collection for Pathogens (NCCP) of Kyungpook National University Hospital.

TABLE 2

| Bacterium | Number of isolates | Source | MIC (ug/mL) |
| --- | --- | --- | --- |
| *Klebsiella pneumoniae* | 20 | NCCP | 450 |
| *Staphylococcus aureus* | 20 | NCCP | 450 |
| *Escherichia coli* | 20 | NCCP | 450 |
| *Pseudomonas aeruginosa* | 20 | NCCP | 450 |
| *Enterococcus faecium* | 20 | NCCP | 450 |

Meanwhile, examples of preparations using the protein of the present invention are exemplified below, but this is not intended to limit the present invention, but is intended to be described in detail.

Formulation Example 1: Preparation of Powder

Recombinant protein Ablysin 300 mg
Lactose 100 mg
Talc 10 mg
The above ingredients are mixed and filled in an airtight cloth to prepare a powder.

Formulation Example 2: Preparation of Tablets

Recombinant protein Ablysin 300 mg
Corn starch 100 mg
Lactose 100 mg
Magnesium stearate 2 mg
After mixing the above ingredients, tablets are prepared by compressing according to a conventional tablet preparation method.

Formulation Example 3: Preparation of Capsules

Recombinant protein Ablysin 300 mg
Crystalline cellulose 3 mg
Lactose 14.8 mg
Magnesium stearate 0.2 mg
According to a conventional capsule preparation method, the above ingredients are mixed and filled into gelatin capsules to prepare a capsule.

Formulation Example 4: Preparation of Injection Formulation

Recombinant protein Ablysin 300 mg
Mannitol 180 mg
Sterile distilled water for injection 2974 mg
$Na_2HPO_4 \cdot 2H_2O$ 26 mg
According to a conventional injection preparation method, it is prepared with the above ingredients per ampoule (2).

Formulation Example 5: Preparation of Liquid Formulation

Recombinant protein Ablysin 300 mg
Isomerized sugar 10 g
Mannitol 5 g
Purified water appropriate amount
According to a conventional preparation method of liquid formulation, each ingredient is added to purified water to dissolve it, lemon zest is added and the above ingredients are mixed, purified water is added to adjust the total amount to 100, then filled in a brown bottle for sterilization to prepare liquid formulation.

Formulation Example 6: Preparation of Food Additives

A milk composition according to the present invention was prepared by adding 1% (w/v) of the recombinant protein Ablysin of the present invention to 200 mL of commercially available S-manufactured milk.

Formulation Example 7: Preparation of Feed Additive

A feed additive was prepared according to the method for producing a feed additive by mixing 100 g of the recombinant protein Ablysin of the present invention and an appropriate amount of an excipient.

Formulation Example 8: Feed Preparation

A feed was prepared according to a conventional feed preparation method by mixing recombinant protein of the present invention Ablysin of 50 g, mushroom medium of 200 g, wheat brp of 30 g, beet pulp of 50 g, rice DDGS (Distillers Dried Grains with Solubles) of 220 g, corn flakes of 200 g, whole soybean of 40 g, starch pulp of 100 g, corn silage of 200 g, corn cob of 180 g, bean-curd dregs of 400 g, ryegrass of 323 g, geolite of 14 g and tapioca of 40 g.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The scope of the present invention is indicated by the claims to be described later, and all changes or modified forms derived from the meaning and scope of the claims and their equivalent concepts should be interpreted as being included in the scope of the present invention.

---

The invention claimed is:

1. A method of preventing or treating a multidrug-resistant pathogenic bacterial infectious disease, comprising:

providing a pharmaceutical composition comprising an Ablysin protein, wherein the Ablysin protein comprises the amino acid sequence of SEQ ID NO: 1 as an active ingredient; and administering the pharmaceutical composition to a subject in need thereof, wherein the multidrug-resistant pathogenic bacterial infectious disease is an infection caused by *Acinetobacter baumannii*.

* * * * *

SEQUENCE LISTING

```
<160> NUMBER OF SEQ ID NOS: 6

<210> SEQ ID NO 1
<211> LENGTH: 252
<212> TYPE: PRT
<213> ORGANISM: Acinetobacter baumannii

<400> SEQUENCE: 1

Met Thr Lys Leu Ala Lys Thr Phe Ser Ala Pro Arg Tyr Asn Thr Leu
1               5                   10                  15

Ile Gly Ile Val Leu Ala Cys Val Met Gly Val Leu Thr Tyr Phe Gly
                20                  25                  30

Leu Phe Tyr Gln Gln Lys Ala Ile Ala Gln Asp Tyr Pro Val Gln Gly
            35                  40                  45

Phe Asp Val Ser His His Gln Glu Asn Ile Asn Trp Lys Lys Ile Ser
    50                  55                  60

Pro Lys Lys Phe Gln Phe Val Tyr Leu Lys Ala Thr Glu Gly Gly Asp
65                  70                  75                  80

Tyr Lys Asp Pro Lys Phe Gln Glu Asn Trp Leu Lys Ala Arg Glu His
                85                  90                  95

Gly Phe His Val Gly Ala Tyr His Phe Tyr Arg Leu Cys Arg Asp Gly
            100                 105                 110

Lys Thr Gln Ala Glu Asn Phe Ile Ser Thr Val Pro Asn Lys Ala Asp
        115                 120                 125

Ala Leu Pro Pro Val Ile Asp Leu Glu Tyr Asp Ser Asn Cys Ile Asn
    130                 135                 140

Ser His Thr Lys Glu Gln Leu Leu Lys Glu Ile Gly Ile Met His Asp
145                 150                 155                 160

Ser Leu Lys His His Tyr Gly Lys Gln Pro Ile Phe Tyr Ile Ser Lys
                165                 170                 175

Thr Phe Tyr His Ile Val Leu Ile Gly Ser Phe Pro His Thr Pro Leu
            180                 185                 190

Trp Val Arg Asp Tyr Glu Gly Lys Pro Glu Leu Lys Asp Lys Arg Lys
        195                 200                 205

Trp Leu Phe Trp Gln His Ser Asn Gln Gly Lys Ile Glu Gly Ile Thr
    210                 215                 220

Lys Pro Val Asp Leu Asn Val Tyr Glu Gly Ser Val Lys Glu Trp His
225                 230                 235                 240
```

Gln Phe Leu Gln Gln Gln Gly Ile Val Lys Ala Gln
            245                 250

<210> SEQ ID NO 2
<211> LENGTH: 759
<212> TYPE: DNA
<213> ORGANISM: Acinetobacter baumannii

<400> SEQUENCE: 2

| | | | | | |
|---|---|---|---|---|---|
| atgaccaagc | tggcaaaaac | cttttctgca | ccacgctaca | atacccttat | tgggattgtt | 60 |
| ttagcttgtg | ttatgggggt | tctcacctac | ttcggtctgt | tctaccagca | aaaagctatt | 120 |
| gctcaagatt | acccagttca | aggctttgat | gtctctcacc | atcaagaaaa | tattaactgg | 180 |
| aaaaaaatat | cacccaaaaa | attccagttc | gtctatttaa | aagcgactga | aggcggtgat | 240 |
| tataaagatc | caaaatttca | agaaaactgg | ttaaaagcac | gcgaacatgg | ctttcatgtc | 300 |
| ggggcttatc | attttatcg | tttatgtcgt | gatggcaaaa | cacaagctga | aaattttatt | 360 |
| tcaaccgtac | ccaacaaagc | tgatgccctt | cctcccgtta | ttgatctgga | atatgacagc | 420 |
| aactgtatta | attctcatac | caagaacaa | ttacttaaag | aaataggcat | catgcatgac | 480 |
| agcttaaagc | atcattatgg | taaacagcct | atctttata | tttccaaaac | ttttaccat | 540 |
| attgtattaa | taggtagttt | ccctcataca | cctctttggg | tcagagatta | cgaagggaaa | 600 |
| cctgagctga | agacaagcg | aaaatggctc | ttttggcagc | atagtaatca | aggtaaaatt | 660 |
| gaaggcatca | ccaagccagt | agacttaaat | gtttatgaag | gttcagtcaa | agaatggcac | 720 |
| caattttac | agcagcaagg | catcgtgaaa | gcacaatga | | | 759 |

<210> SEQ ID NO 3
<211> LENGTH: 43
<212> TYPE: DNA
<213> ORGANISM: Artificial Sequence
<220> FEATURE:
<223> OTHER INFORMATION: Primer

<400> SEQUENCE: 3
catcatcatc atcatcatgg tatgaccaag ctggcaaaaa cct      43

<210> SEQ ID NO 4
<211> LENGTH: 43
<212> TYPE: DNA
<213> ORGANISM: Artificial Sequence
<220> FEATURE:
<223> OTHER INFORMATION: Primer

<400> SEQUENCE: 4
cgttctgatt taatctgtat cattgtgctt tcacgatgcc ttg      43

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
tgatacagat taaatcagaa cgcagaagcg      30

<210> SEQ ID NO 6
<211> LENGTH: 28
<212> TYPE: DNA
<213> ORGANISM: Artificial Sequence

```
<220> FEATURE:
<223> OTHER INFORMATION: Primer

<400> SEQUENCE: 6
accatgatga tgatgatgat gagaaccc                                              28
```